United States Patent [19]

Schindler et al.

[11] 4,256,561

[45] Mar. 17, 1981

[54] ELECTROCHEMICAL MEASURING ELECTRODE

[75] Inventors: Johannes G. Schindler, Marburg; Wilfried Schal, Bad Homburg, both of Fed. Rep. of Germany

[73] Assignee: Dr. Eduard Fresenius Chemisch-pharmazeutische Industrie KG, Apparatebau KG, Bad Homburg, Fed. Rep. of Germany

[21] Appl. No.: 37,232

[22] Filed: May 8, 1979

[30] Foreign Application Priority Data

May 10, 1978 [DE] Fed. Rep. of Germany ....... 2820474

[51] Int. Cl.³ ............................................. G01N 27/30
[52] U.S. Cl. ............................................. 204/195 M
[58] Field of Search ...................... 204/195 M, 195 G; 128/635

[56] References Cited

U.S. PATENT DOCUMENTS

| 3,607,710 | 9/1971 | Farren et al. | 204/195 M |
| 3,718,569 | 2/1973 | Petersen et al. | 204/195 G |
| 3,787,307 | 1/1974 | Schwab et al. | 204/195 G |
| 3,856,649 | 12/1974 | Genshaw et al. | 204/195 M X |
| 3,926,764 | 12/1975 | Ruzicka et al. | 204/195 M X |
| 4,111,777 | 9/1978 | Dobson et al. | 204/195 M |

FOREIGN PATENT DOCUMENTS 2251287 4/1973 Fed. Rep. of Germany ...... 204/195 M

*Primary Examiner*—G. L. Kaplan
*Attorney, Agent, or Firm*—Omri M. Behr; Martin Sachs

[57] ABSTRACT

An electrochemical measuring electrode has an ion-selective membrane and direct potential take off via an electron conductor. A diffusion barrier layer is provided between the membrane and the electron conductor for the purpose of reducing or eliminating the sensitivity to faults which can be caused by the presence of gases in a medium which is to be analyzed and into which the sensor is introduced. The diffusion barrier preferably comprises an ion-conducting solid-state body having a high diffusion resistance to oxygen.

9 Claims, 1 Drawing Figure

U.S. Patent   Mar. 17, 1981   4,256,561
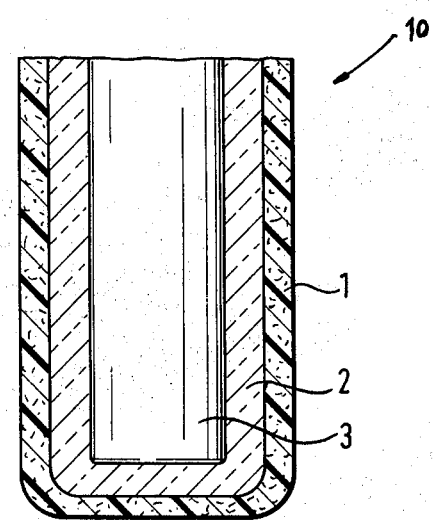

ELECTROCHEMICAL MEASURING ELECTRODE

BACKGROUND OF THE INVENTION

1. Field of the Invention

The invention relates to electrochemical measuring electrodes which are used in aqueous liquids for the purpose of measuring the activity of certain ions.

2. Description of the Prior Art

Electrochemical measuring sensors generally are used in the form of an electrode, which is made selective to certain types of ions, plus a reference electrode and a voltmeter having a very high input resistance. The voltage indicated by the voltmeter is a measure of the activity of the ions being measured in accordance with the known Nernst equation.

Many different types of construction are used in fabricating. The common operating principle is based upon the fact that a membrane is used which is selective with respect to the test ions. This membrane is in contact with the medium to be analyzed while on the other side of the membrane the electrical potential caused by the activity of the test ions is taken off. An enzyme system may be provided in front of the membrane in order to convert certain molecules, thereby releasing ions in an appropriate quantity to produce an electrical potential across the membrane.

The ion conduction takes place in most ion-selective electrodes via an internal electrolyte, i.e., a space filled with an electrolyte liquid is located at the rear side of the membrane and a metallic electrically conducting electrode dips into the liquid electrolyte. However, ion-selective electrodes with direct electrical conduction have been proposed in which the rear side of the ion-selective membrane is in direct contact with the metal or with a conducting electrode made from graphite (c.f. H. Hirata and K. Date: Cooper (I) sulphide-impregnated silicone rubber membranes as selective electrodes for copper (II) ions, Talanta, Vol. 17 (1970), pp. 883–887; and U.S. Pat. No. 3 607–710).

The electrolytic conduction of the membrane potential is characterized by good stability which can probably be attributed to the fact that at the rear side of the membrane, where the ions are conducted, a fixed conduction path is defined. When using membranes of fairly high elasticity (for example plastic membranes) together with a liquid conducting electrolyte a major disadvantage occurs. This disadvantage occurs because of the considerable interference effect introduced by the fluctuations in pressure occuring in the test medium. Fixed direct electrical conduction electrodes do not suffer from this disadvantage and fluctuations in pressure in the measuring system do not therefore have any effect in practice on the measured test value. This is probably due to the fact that the fixed metallic conducting electrode contact for the membrane material acts as a fixed mechanical abutment so that yielding of the membrane under the action of pressure is prevented. On the other hand, these electrodes, more particularly electrodes utilized with plastic membranes, show a considerable interference action as the result of oxygen and other gases.

SUMMARY OF THE INVENTION

The primary object of the present invention is to provide an electrochemical measuring sensor which retains the advantage of the fixed direct electrical conduction electrodes, which are not sensitive to pressure and moreover, to provide a characteristic which makes it non-sensitive with respect to oxygen and other gases as are the electrodes known in the prior art that utilize a fluid electrolyte and a flexible membrane.

The cause of the dependency on oxygen for measurements with electrodes having ion-selective plastic membranes and fixed direct contact electrical conduction electrodes has not heretofore been clarified. In order to solve the problem in accordance with the principles of the instant invention, it was assumed that the measurement utilized a reaction of the oxygen diffusing through the membrane at the boundary surface to the electron conducting contact. In order to suppress this reaction, the oxygen must be prevented from penetrating up to the boundary of the metallic conducting element. The accuracy of this assumption has been confirmed by a series of experiments.

Several experiments were carried out with different combinations of material and arrangements in several layers in which the dependency on oxygen was investigated. By inserting an intermediate layer having a high diffusion resistance to oxygen the sensitivity to oxygen was considerably reduced or completely eliminated.

Accordingly, the present invention provides an electrochemical measuring electrode having an ion-selective membrane, a fixed direct electrical conduction contact and at least one layer acting as a diffusion barrier inserted between the membrane and the electrical conductor for the purpose of reducing or eliminating the sensitivity to faults by means of gases contained in the test medium.

Preferably, the diffusion barrier comprises an ion-conducting solid-state body having a high diffusion resistance to oxygen.

BRIEF DESCRIPTION OF THE DRAWING

An embodiment of an electrode measuring sensor according to the principles of the present invention, is shown schematically in the single figure of the drawing.

DESCRIPTION OF THE PREFERRED EMBODIMENT

An electrode 10 includes an ion-selective membrane 1, an intermediate layer constructed as a diffusion barrier having a low permeability to oxygen 2 and a metallic electrical conducting contact 3.

The membrane 1, which determines the selectivity characteristics of the electrode can comprise, for example, an organic polymer having embedded therein ion-active substances in the form of organic carrier molecules, ion ligands, ion exchangers, et. The ion-active substances may be present in a molecular or—in the case of non-soluble substances—in a very corpuscular distribution. Membrane materials of this type with highly selective characteristics for certain ions are known in many cases. A typical example of the type first mentioned are membranes with valinomycin in PVC as a matrix which have highly selective characteristics for potassium ions. The membranes may contain different additions such as softeners for example and lipophilic anions in order to optimize the characteristics.

Fixed ion conductors are suitable as the diffusion barrier 2 and should exhibit as high as possible a diffusion resistance to gases, more particularly oxygen. Glass and glass-like substances (mixtures of silicates, borosilicates, borates, phosphates) have proved to be particularly favorable for this. The electrical conductivity due to ion conduction is in fact very low in these substances and when using a measuring circuit with a correspondingly high input resistance hardly any restrictions in the ion sensitivity are established if the internal resistance of the electrode is still below the input resistance of the measuring circuit by approximately three orders of magnitude.

The relationship between the ions which determine the electrical conductivity of the diffusion barrier 2 and the type of ion which can be moved in the ion-selective membrane 1 is not important according to the results of the experiments. It is not necessary for the diffusion barrier 2 and the ion-selective membrane to have a common characteristic ion. Thus, an electrode with a diffusion barrier made from a specific sodium-selective glass which is used usually for sodium-selective electrodes, and having an ion-selective membrane 1 made from PVC with a calcium carrier acts like a calcium-selective electrode of normal construction with respect to its ions selectivity. At the boundary surface between the membrane 1 and the diffusion barrier 2 an exchange of charge between the different ions taking part in transportation of the charge may take place and this exchange of charge does not occur towards the outside.

Because of the established mechanism of the effect in general, all ion- conducting solid-state bodies having a high diffusion resistance to oxygen can be considered as a diffusion barrier. From this salts, more particularly silver halides and phosphates and silicates which are formed from mixtures of pulverized metal oxides and phosphoric acid or water glass, and moreover different cements, belong to this category.

The selection of the electrically conducting contact 3 depends in the first instance on the fact that a solid connection between its material and the substance of the diffusion barrier is to be achieved so that for example the thermal coefficient of expansion of the metal must be matched to those of the diffusion barrier. If these and other points of view which are usual in technology with respect to mutual compatibility of the materials in contact with each other are taken into account then a wide selection of different metals and possibly also other electrically-conducting materials may be used at this point. According to the results of the test carried out it is not important whether the ion conductor used as a diffusion barrier contains a metal ion which is the same as the metal used as an electrical conduction contact. In particular, it is advantageous if very fine wires made from platinum for example are used since they facilitate miniaturization of the measuring electrode to the smallest space possible so that a larger number can be housed in a catheter for different materials of sensitive measuring electrodes.

EXAMPLE 1

An ion-selective glass of the type NA made by the Messrs. Ingold (Frankfurt) was fused on to a platinum wire of 0.2 mm diameter at the largest point, and preferably not greater than 10 mm in diameter. Thereupon a covering layer made from PVC was formed according to known methods into which covering layer a synthetic neutral calcium carrier was embedded besides softeners and lipophylic anions. The synthetic neutral carrier is described in D. Ammann et al: Synthetic Neutral Carriers for Cations, in M. Kessler et al: Ion and Enzyme Electrodes in Biology and Medicine. Published by Urban and Schwarzenberg, Munich, Berlin, Vienna (1976), 22. The selectivity and sensitivity for calcium was not restricted by the intermediate layer made from glass but the sensitivity to oxygen which occurred in a disturbing manner without this intermediate layer could no longer be observed.

EXAMPLE 2

A conventional enamel for craftwork was fluxed on to a copper wire of 1.0 mm diameter and coated with membranes made from PVC into which an electrically charged ion ligand for $Ca^{++}$ was embedded as an electroactive phase for anions. The results were the same as in Example 1.

EXAMPLE 3

Layers of salt were applied to metal wires of different diameter, for example platinum wires and subsequently melted on to these metal wires so that a glass-flow-like air-tight coating was formed. In preferred manner silver chloride was used for this. Also, in this case, there were selectivities which were outstanding in relation to different ion-selective membranes on a PVC base and independent of the presence of oxygen or other gases.

EXAMPLE 4

Instead of enamel (Example 2) a conventional dental cement was used, for example copper cement made by De Trey of Waldshut, a zinc oxyphosphate cement with the addition of copper or Harvard cement. Here too the same results were achieved.

The principle of the electrodes described having an inserted ion-conducting layer which suppresses the diffusion of gases out of the medium to be analyzed to the electrically conducting contact may be used in many known electrode constructions. Furthermore, it is possible to use electrodes of this type in a known manner as a component of a gas-sensitive or enzymatic measuring sensor.

We claim:

1. An electrochemical measuring electrode comprising:
    (a) an electrically conductive contact;
    (b) an ion selectively active organic polymer membrane covering said contact; and
    (c) at least one solid ion conducting diffusion barrier comprising a solid body having a high diffusion resistance to oxygen selected from the group consisting of a vitreous material, a dental cement, and a fused layer of salt, disposed between said membrane and said contact.

2. A measuring electrode according to claim 1, wherein the diffusion barrier is a vitreous material.

3. A measuring electrode according to claim 1, wherein the diffusion barrier comprises a fused layer of a salt.

4. A measuring electrode according to claim 1, wherein the diffusion barrier comprises a dental cement.

5. A measuring electrode according to claim 4 wherein said dental cement consists substantially of zinc oxyphosphate.

6. A measuring electrode according to claim 1, wherein the ion-selectively active membrane is made from PVC and contains an electrically neutral ion carrier.

7. A measuring electrode according to claim 1, wherein the ion-selectively active membrane is made from PVC and contains an electrically charged ion ligand.

8. A measuring electrode accoding to claim 1, wherein the ion-selectively active membrane comprises at least one organic polymer and at least one ion-selectively active component embedded in molecular or corpuscular distribution in said polymer, said ion-selectively active components being selected from the group consisting of organic carrier molecules, selective and charged ligands, and ion exchangers.

9. A measuring electrode in accordance with claim 1 wherein the electrically conductive contact is a metallic contact and wherein the diffusion barrier is a fused salt layer of a salt having a cation derived from a metal different from the metal in the electrically conductive contact.

* * * * *